US009439421B2

(12) United States Patent
Locklin

(10) Patent No.: US 9,439,421 B2
(45) Date of Patent: *Sep. 13, 2016

(54) PERMANENT ATTACHMENT OF AMMONIUM AND GUANIDINE-BASED ANTIMICROBIALS TO SURFACES CONTAINING -OH FUNCTIONALITY

(75) Inventor: Jason J. Locklin, Bogart, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 136 days.

This patent is subject to a terminal disclaimer.

(21) Appl. No.: 14/114,913

(22) PCT Filed: Aug. 2, 2012

(86) PCT No.: PCT/US2012/049258
§ 371 (c)(1),
(2), (4) Date: Oct. 31, 2013

(87) PCT Pub. No.: WO2013/019918
PCT Pub. Date: Feb. 7, 2013

(65) Prior Publication Data
US 2014/0179876 A1 Jun. 26, 2014

Related U.S. Application Data

(60) Provisional application No. 61/514,966, filed on Aug. 4, 2011, provisional application No. 61/539,551, filed on Sep. 27, 2011.

(51) Int. Cl.
| | | |
|---|---|---|
| C08F 8/34 | (2006.01) |
| C08F 283/04 | (2006.01) |
| C08G 63/00 | (2006.01) |
| C08B 1/00 | (2006.01) |
| C07C 309/00 | (2006.01) |
| A01N 41/04 | (2006.01) |
| A01N 33/12 | (2006.01) |
| A01N 41/02 | (2006.01) |
| A01N 41/10 | (2006.01) |
| A01N 47/44 | (2006.01) |
| A01N 55/00 | (2006.01) |
| A01N 55/02 | (2006.01) |

(52) U.S. Cl.
CPC ............... *A01N 41/04* (2013.01); *A01N 33/12* (2013.01); *A01N 41/02* (2013.01); *A01N 41/10* (2013.01); *A01N 47/44* (2013.01); *A01N 55/00* (2013.01); *A01N 55/02* (2013.01)

(58) Field of Classification Search
CPC ...... A01N 33/12; A01N 41/04; A01N 55/00; A01N 47/44; A01N 41/00; A01N 25/10; A01N 55/02; A01N 25/34; A01N 41/02
USPC ........... 525/333.9, 420, 437; 536/56; 562/36
See application file for complete search history.

(56) References Cited

U.S. PATENT DOCUMENTS

| | | | |
|---|---|---|---|
| 3,697,402 A | 10/1972 | Clifton et al. |
| 5,714,360 A | 2/1998 | Swan et al. |
| 7,709,544 B2 | 5/2010 | Doyle et al. |
| 8,114,319 B2 | 2/2012 | Davis et al. |
| 8,183,540 B2 | 5/2012 | Ward et al. |
| 8,876,914 B2* | 11/2014 | Locklin .............. C08G 73/0226 525/412 |
| 8,968,421 B2* | 3/2015 | Locklin .................. A01N 41/02 525/412 |
| 2006/0105012 A1 | 5/2006 | Chinn et al. |
| 2006/0135639 A1 | 6/2006 | Singh |
| 2006/0147413 A1 | 7/2006 | Alferieve et al. |
| 2006/0148982 A1 | 7/2006 | Ijeoma et al. |
| 2007/0054119 A1 | 3/2007 | Garstecki et al. |
| 2007/0231291 A1 | 10/2007 | Huang et al. |
| 2008/0025503 A1 | 1/2008 | Choi et al. |
| 2008/0214421 A1 | 9/2008 | Zhao et al. |
| 2009/0196826 A1 | 8/2009 | Gao et al. |
| 2010/0227790 A1 | 9/2010 | Mayer et al. |
| 2011/0081643 A1 | 4/2011 | Fournier-Bidoz et al. |
| 2012/0094007 A1 | 4/2012 | Fehr et al. |
| 2013/0183246 A1 | 7/2013 | Wang et al. |

FOREIGN PATENT DOCUMENTS

| | | | |
|---|---|---|---|
| WO | 2010096444 A2 | 8/2010 |
| WO | WO 2010096444 | * 8/2010 |
| WO | 2011139649 A2 | 11/2011 |

OTHER PUBLICATIONS

Office Action in related Chinese Application No. 201080008259.0 dated Jun. 18, 2013.
Extended European Search Report dated Oct. 18, 2013.
The International Search Report and Written Opinion dated Sep. 16, 2010.
Goyal; Nanoscale Approaches for Biomolecule Separtion and Detection. Master in Science in Biomedical Engineering Requirement—Graduate School of The University of Texas at Arlington. Dec. 2009.
Dendukuri, et al.; The Synthesis and Assembly of Polymeric Microparticles Using Microfluidics. Advanced Review. vol. 21, 2009. 2009 Wiley-VCH Verlag GmbH & Co. KGaA, Weinheim pp. 4071-4086.
Yuan, et al.; Large scale manufacture of magnetic polymer particles using membranes and microfluidic devices. China Particuology. vol. 5, 2007. pp. 26-42.

(Continued)

*Primary Examiner* — William Cheung
(74) *Attorney, Agent, or Firm* — Thomas|Horstemeyer, LLP

(57) ABSTRACT

Embodiments of the present disclosure relate to compounds, methods of making compositions (used as a linker or a linker moiety), structures having the compound covalently bonded to the surface of the structure, methods of attaching the compound to the surface of the structure having —OH functionality (e.g., $C_{alkyl}$—OH), methods of decreasing the amount of microorganisms formed on a structure, and the like.

17 Claims, No Drawings

(56) References Cited

OTHER PUBLICATIONS

Chen, et al., Microfluidic Assembly of Magnetic Hydrogel Particles with Uniformly Anisotropic Structure. Advanced Review. vol. 21, 2009. 2009 Wiley-VCH Verlag GmbH & Co. KGaA, Weinheim pp. 3201-3204.

Hwang, et al., Microfluidic-based synthesis of non-spherical magnetic hydrogel microparticles. Lab on a Chip. vol. 8, 2008. The Royal Society of Chemistry 2008 pp. 1640-1647.

Shum, et al.; Droplet Microfluidics for Fabrication of Non-Spherical Particles. Macromolecular Rapid Communications. vol. 32, 2010. 2010 Wiley-VCH Verlag GmbH & Co. KGaA, Weinheim. pp. 108-118.

Wang, et al.; Fabrication of Monodisperse Toroidal Particles by Polymer Solidification in Microfluidics. ChemPhysChem. vol. 10, 2009. 2009 Wiley-VCH Verlag GmbH & Co. KGaA, Weinheim. pp. 641-645.

Examination Report on related New Zealand Application No. 602911 dated Jun. 18, 2013.

The International Preliminary Report on Patentability dated Nov. 8, 2012.

The International Search Report and Written Opinion dated Jan. 19, 2012.

The International Search Report and Written Opinion dated Feb. 28, 2013.

\* cited by examiner

PERMANENT ATTACHMENT OF AMMONIUM AND GUANIDINE-BASED ANTIMICROBIALS TO SURFACES CONTAINING -OH FUNCTIONALITY

CROSS-REFERENCE TO RELATED APPLICATION

This application is the 35 U.S.C. §371 national stage of PCT application having serial number PCT/US2012/049258, filed on Aug. 2, 2012. This application also claims priority to and benefit of U.S. Provisional Application No. 61/514,966 filed on Aug. 4, 2011, and U.S. Provisional Application No. 61/539,551, filing date Sep. 27, 2011, each incorporated by reference in their entireties.

BACKGROUND

Covalent attachment of antimicrobial agents to structures such as fabrics can be challenging. Thus, solutions for attaching antimicrobial agents to structures are actively being pursued.

SUMMARY

Embodiments of the present disclosure relate to compounds, methods of making compositions (used as a linker or a linker moiety), structures having the compound covalently bonded to the surface of the structure, methods of attaching the compound to the surface of the structure having —OH functionality (e.g., $C_{alkyl}$—OH), methods of decreasing the amount of microorganisms formed on a structure, and the like.

An embodiment of the compound, among others, includes: an antimicrobial moiety having a structure:

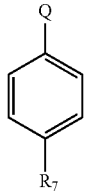

Q is X or R8-X; R8 is selected from: O, NR13, a substituted or unsubstituted aliphatic group, an S group, a SR13 group, a substituted or unsubstituted aryl group, and a substituted or unsubstituted heteroaryl group; R13 is selected from the group consisting of: a substituted or unsubstituted aliphatic group, a substituted or unsubstituted aryl group, and a substituted or unsubstituted heteroaryl group; R7 is selected from one of:

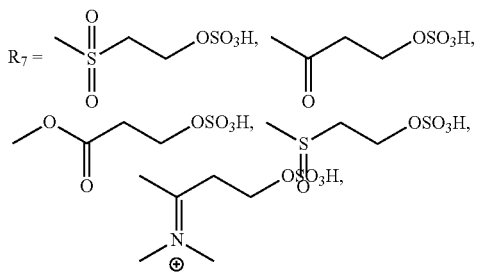

X is an antimicrobial agent (AM).

An embodiment of the article, among others, includes: an antimicrobial moiety, such as those described herein, bonded to the article.

DETAILED DESCRIPTION

Before the present disclosure is described in greater detail, it is to be understood that this disclosure is not limited to particular embodiments described, as such may, of course, vary.

It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features that may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, polymer chemistry, biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmospheres. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

The term "substituted" refers to any one or more hydrogens on the designated atom that can be replaced with a selection from the indicated group, provided that the designated atom's normal valence is not exceeded, and that the substitution results in a stable compound. In an embodiment, the indicated group can include in or more halogens, aliphatic groups, and the like.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon chain and a substituted saturated aliphatic hydrocarbon chain which may be straight, branched, or cyclic, having 1 to 20 carbon atoms, where the stated range of carbon atoms includes each intervening integer individually, as well as sub-ranges. Examples of alkyl groups include, but are not limited to, methyl, ethyl, i-propyl, n-propyl, n-butyl, t-butyl, pentyl, hexyl, septyl, octyl, nonyl, decyl, and the like. The substitution can be with a halogen, for example.

As used herein, "alkenyl" or "alkenyl group" refers to an aliphatic hydrocarbon which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "alkynyl" refers to straight or branched chain hydrocarbon groups, containing at least one triple carbon to carbon bond having 2 to 20 carbon atoms, wherein the stated range of carbon atoms includes each intervening integer individually, as well as sub-ranges. An alkynyl group can be optionally substituted, unless stated otherwise, with one or more groups.

The term "arylalkyl" refers to an arylalkyl group wherein the aryl and alkyl are as herein described. Examples of arylalkyl include, but are not limited to, -phenylmethyl, -phenylethyl, -phenylpropyl, -phenylbutyl, and -phenylpentyl.

The term "aryl" refers to aromatic homocyclic (i.e., hydrocarbon) mono-, bi- or tricyclic ring-containing groups preferably having 6 to 12 members such as phenyl, naphthyl and biphenyl. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, etc., where optionally one or more pair of substituents together with the atoms to which they are bonded form a 3 to 7 member ring.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

The term "substituted," as in "substituted alkyl", "substituted cycloalkyl," "substituted cycloalkenyl," substituted aryl," substituted biaryl," "substituted fused aryl" and the like means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl group in which one or more hydrogens are substituted by halogen radicals. Examples of haloalkyl include, but are not limited to, trifluoromethyl, trichloromethyl, pentafluoroethyl, and pentachloroethyl.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl group in which one or more hydrogens are substituted by halogen radicals. Examples of haloalkyl include, but are not limited to, trifluoromethyl, trichloromethyl, pentafluoroethyl, and pentachloroethyl.

As used herein, the term "fiber" refers to filamentous material that can be used in fabric and yarn as well as textile fabrication and include —OH functionality inherently or with a functional layer. One or more fibers can be used to produce a fabric or yarn. Fibers include, without limitation, materials such as cellulose, fibers of animal origin (e.g., alpaca, angora, wool and vicuna), hemicellulose, lignin, polyesters, polyamides, rayon, modacrylic, aramids, polyacetates, polyxanthates, acrylics and acrylonitriles, polyvinyls and functionalized derivatives, polyvinylidenes, PTFE, latex, polystyrene-butadiene, polyethylene, polyacetylene, polycarbonates, polyethers and derivatives, polyurethane-polyurea copolymers, polybenzimidazoles, silk, lyocell, carbon fibers, polyphenylene sulfides, polypropylene, polylactides, polyglycolids, cellophane, polycaprolactone, "M5" (poly{diimidazo pyridinylene (dihydroxy) phenylene}), melamine-formadehyde, plastarch, PPOs (e.g., Zylon®), polyolefins, and polyurethane. In an embodiment, the fiber is made of polyethylene, polyester, aramid, polyamide, cellulose, hemicellulose, acrylic, and latex.

The term "textile article" can include garments, fabrics, carpets, apparel, furniture coverings, drapes, upholstery, bedding, automotive seat covers, fishing nets, rope, articles including fibers (e.g., natural fibers, synthetic fibers, and combinations thereof), articles including yarn (e.g., natural fibers, synthetic fibers, and combinations thereof), and the like.

The term "antimicrobial characteristic" refers to the ability to kill and/or inhibit the growth of microorganisms. A substance having an antimicrobial characteristic may be harmful to microorganisms (e.g., virus, bacteria, fungi, protozoans, algae, and the like). A substance having an antimicrobial characteristic can kill the microorganism and/or prevent or substantially prevent the growth or reproduction of the microorganism. "Antimicrobial" includes antibacterial and antiviral.

The term "antiviral characteristic" refers to the ability to kill and/or inhibit the growth of a virus. A substance having an antiviral characteristic may be harmful to a virus. A substance having an antiviral characteristic can kill the virus and/or prevent or substantially prevent the replication or reproduction of the virus.

Viruses which may be inhibited by compounds of the present disclosure include, but are not limited to: Adenoviruses, Coronaviruses, Cytomegalovirus, Enteroviruses, Epstein-Barr virus, Herpes simplex virus, Hepatitis viruses, Human Immunodeficiency virus, Human Parvoviruses, Influenza viruses, Morbillivirus, Mumps virus, Norwalk viruses, Papillomaviruses, Paromyxovirus, Poxvirus, Rabies virus, Reoviruses, Rotaviruses, Rubella virus, Respiratory Synctial virus, Rhinoviruses, Varicella zoster virus, and the like.

The term "antibacterial characteristic" refers to the ability to kill and/or inhibit the growth of bacteria. A substance having an antibacterial characteristic may be harmful to bacteria. A substance having an antibacterial characteristic can kill the bacteria and/or prevent or substantially prevent the replication or reproduction of the bacteria.

The terms "bacteria" or "bacterium" include, but are not limited to, Gram positive and Gram negative bacteria. Bacteria can include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anabaena affinis* and other cyanobacteria (including the *Anabaena, Anabaenopsis, Aphanizomenon, Camesiphon, Cylindrospermopsis, Gloeobacter Hapalosiphon, Lyngbya, Microcystis, Nodularia, Nostoc, Phormidium, Planktothrix, Pseudoanabaena, Schizothrix, Spirulina, Trichodesmium,* and *Umezakia* genera) *Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania lgnavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella*. Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies paratuberculosis, *Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides,* and other *Nocardia* species, *Streptococcus viridans* group, *Peptococcus* species, *Peptostreptococcus* species, *Actinomyces israelii* and other *Actinomyces* species, and *Propionibacterium acnes, Clostridium tetani, Clostridium botulinum,* other *Clostridium* species, *Pseudomonas aeruginosa,* other *Pseudomonas* species, *Campylobacter* species, *Vibrio cholera, Ehrlichia* species, *Actinobacillus pleuropneumoniae, Pasteurella haemolytica, Pasteurella multocida,* other *Pasteurella* species, *Legionella pneumophila,* other *Legionella* species, *Salmonella typhi,* other *Salmonella* species, *Shigella* species *Brucella abortus,* other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi,* other *Hemophilus* species, *Yersinia pestis, Yersinia enterolitica,* other *Yersinia* species, *Escherichia coli, E. hirae* and other *Escherichia* species, as well as other *Enterobacteria, Brucella abortus* and other *Brucella* species, *Burkholderia cepacia, Burkholderia pseudomallei, Francisella tularensis, Bacteroides fragilis, Fudobascterium nucleatum, Provetella* species, and *Cowdria ruminantium,* or any strain or variant thereof. The Gram-positive bacteria may include, but is not limited to, Gram positive Cocci (e.g., *Streptococcus, Staphylococcus,* and *Enterococcus*). The Gram-negative bacteria may include, but is not limited to, Gram negative rods (e.g., Bacteroidaceae, Enterobacteriaceae, Vibrionaceae, Pasteurellae and Pseudomonadaceae). In an embodiment, the bacteria can include *Mycoplasma pneumoniae*.

The term "protozoan" as used herein includes, without limitations flagellates (e.g., *Giardia lamblia*), amoeboids (e.g., *Entamoeba* histolitica), and sporozoans (e.g., *Plasmodium knowlesi*) as well as ciliates (e.g., *B. coli*). Protozoan can include, but it is not limited to, *Entamoeba coli, Entamoeabe histolitica, lodoamoeba buetschlii, Chilomastix meslini, Trichomonas vaginalis, Pentatrichomonas homini, Plasmodium vivax, Leishmania braziliensis, Trypanosoma cruzi, Trypanosoma brucei,* and *Myxoporidia*.

The term "algae" as used herein includes, without limitations microalgae and filamentous algae such as *Anacystis nidulans, Scenedesmus* sp., *Chlamydomonas* sp., *Clorella* sp., *Dunaliella* sp., *Euglena* sp., *Prymnesium* sp., *Porphyridium* sp., *Synechoccus* sp., *Botryococcus braunii, Ctypthecodinium cohnii, Cylindrotheca* sp., *Microcystis* sp., *isochrysis* sp., *Monallanthus salina, M. minutum, Nannochloris* sp., *Nannochloropsis* sp., *Neochloris oleoabundans, Nitzschia* sp., *Phaeodactylum tricornutum, Schizochytrium* sp.,

*Senedesrnus obliquus*, and *Tetraseirnis sueica* as well as algae belonging to any of *Spirogyra, Cladophora, Vaucheria, Pithophora* and *Enteromorpha* genera.

DISCUSSION

In accordance with the purpose(s) of the present disclosure, as embodied and broadly described herein, embodiments of the present disclosure, in one aspect, relate to compounds, methods of making compositions (used as a linker or a linker moiety), structures having the compound covalently bonded to the surface of the structure, methods of attaching the compound to the surface of the structure having —OH functionality (e.g., $C_{alkyl}$—OH), methods of decreasing the amount of microorganisms formed on a structure, and the like. In an embodiment, the compound (or the compound disposed on a surface) has an antimicrobial characteristic (e.g., kills at least 70%, at least 80%, at least 90%, at least 95%, or at least 99% of the microorganisms (e.g., bacteria, virus, a combination of different types microorganisms) and/or reduces the amount of microorganisms that form or grow on the surface by at least 70%, at least 80%, at least 90%, at least 95%, or at least 99%, as compared to a surface without the compound disposed on the surface). Additional details are described herein.

In an embodiment, the compound can be used to bind to a surface or structure of an article having O—H functionality. In an embodiment, the article can include those that are exposed to microorganisms and/or that microorganisms can grow on such as, without limitation, fibers, fabrics, cooking counters, food processing facilities, kitchen utensils, food packaging, swimming pools, metals, drug vials, medical instruments, medical implants, yarns, fibers, gloves, furniture, plastic devices, toys, diapers, leather, tiles, and flooring materials. In an embodiment, the articles may also include live biologic structures (or surfaces of live biologic structures) such as seeds for agricultural uses, tree limbs, and trunk, as well as teeth.

In an embodiment, the article inherently includes —OH groups on the surface of the structure to interact with the compound, as described below. In an embodiment, the article includes a functionalized layer disposed on the article that includes the —OH groups on the surface to interact with the compound. In an embodiment, the article can include surfaces that inherently include —OH groups on the surface of the article and also can include surfaces that include a functionalized layer disposed on the structure that includes the —OH groups. In an embodiment, the functionalized layer can have a thickness of about 2 nanometers (nm) to 1 micrometer (µm) or about 25 nm to 120 nm.

In an embodiment, the article can include textile articles, fibers, filters or filtration units (e.g., HEPA for air and water), packaging materials (e.g., food, meat, poultry, and the like food packaging materials), plastic structures (e.g., made of a polymer or a polymer blend), glass or glass like structures having a functionalized layer (e.g., includes a —OH group) on the surface of the structure, metals, metal alloys, or metal oxides structure having a functionalized layer (e.g., includes a —OH group) on the surface of the structure, a structure (e.g., tile, stone, ceramic, marble, granite, or the like) having a functionalized layer (e.g., includes a —OH group) on the surface of the structure, and a combination thereof.

In an embodiment, the compound is a linker that can be used to bind to surfaces or structures having $C_{alkyl}$—OH functionality such as fibers. In an embodiment, the fiber can include: a polypropylene fiber, a polyethylene fiber, a polyester fiber, a polyamide fiber, an aramid fiber, a cellulose fiber, a hemicellulose fiber, an acrylic fiber, a latex fiber, and a natural fiber, as well as natural surfaces, or another surface or structure having $C_{alkyl}$—OH functionality.

In an embodiment, the compound has a covalent bond (S—C) that forms between the compound and the surface having a —OH group or a layer on the surface having the —OH group. In other words, the compound can be attached to the surface or the layer on the surface so the bonding is easy and inexpensive to achieve. Once the covalent bond is formed, the compound layer is strongly bound to the surface and can withstand very harsh conditions such as sonication and extended washing steps as well as exposure to harsh environmental conditions (e.g., heat, cold, humidity, lake, river, and ocean conditions (e.g., above and/or under water), and the like).

As mentioned above, the compound can be disposed on a surface to produce an article that includes the compound covalently bonded to the surface of the article. In an embodiment, the method of disposing the compound on the surface of the article includes disposing the compound on the surface using a method such as spraying, dipping, spin coating, drop casting, and the like. In an embodiment, the surface of the article has —OH groups that can interact with the compound. In an embodiment, the article has a layer (also referred to as a "functionalized layer") (e.g., a thin film or self assembling layer) disposed on the surface of the structure. The functionalized layer includes —OH bonds that can interact with the compound.

After the compound is covalently bonded to the surface, the structure has an antimicrobial characteristic that is capable of killing a substantial portion of the microorganisms (e.g., bacteria, virus, or a combination of different types of microorganisms) on the surface of the article and/or inhibits or substantially inhibits the growth of the microorganisms on the surface of the article. The phrase "killing a substantial portion" includes killing at least about 70%, at least about 80%, at least about 90%, at least about 95%, or at least about 99% of the microorganism (e.g., bacteria, virus, or a combination of different types of microorganisms) on the surface that the compound is covalently bonded. The phrase "substantially inhibits the growth" includes reducing the growth of the microorganism (e.g., bacteria, virus, or a combination of different types of microorganisms) by at least about 70%, at least about 80%, at least about 90%, at least about 95%, or at least about 99% of the microorganisms on the surface that the compound is covalently bonded, relative to a structure that does not have the compound disposed thereon.

In an embodiment, the compound can be represented by the following structure.

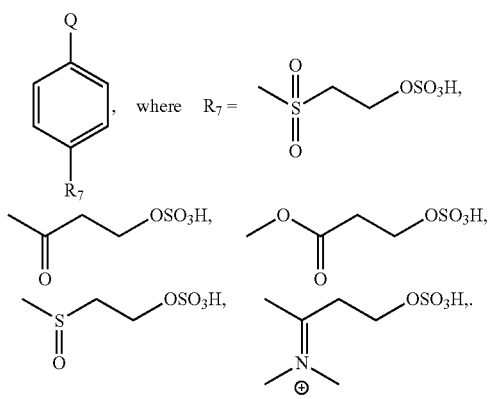

In an embodiment, Q can be X or R8-X. In an embodiment, R8 can be selected from H, O, NR13, a substituted or unsubstituted aliphatic group, an S group, a SR13 group, a substituted or unsubstituted aryl group, and a substituted or unsubstituted heteroaryl group. In an embodiment, R13 can be selected from the group consisting of: H, a substituted or unsubstituted aliphatic group, a substituted or unsubstituted aryl group, and a substituted or unsubstituted heteroaryl group. R7 can be selected from those groups noted above and also those groups can be substituted or unsubstituted.

X can be an antimicrobial agent. In an embodiment, the antimicrobial agent can be one of the following.

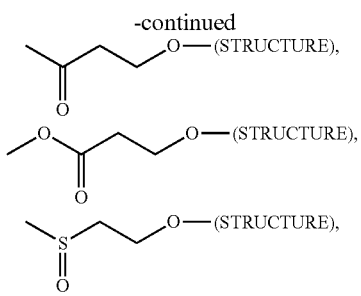

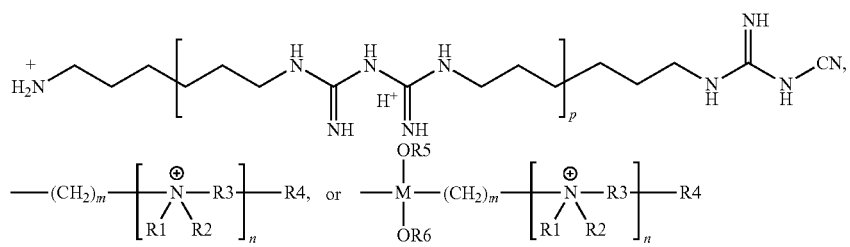

In an embodiment, R1 and R2 can each be independently selected from: H, a substituted or unsubstituted aliphatic group (e.g., an alkyl group (e.g., $CH_3$, $C_2H_5$, $CH_2CF_3$)), a substituted or unsubstituted aryl group (e.g., $C_6H_6$), or and a substituted or unsubstituted heteroaryl group. In an embodiment, R1 and R2 can each be independently selected from $CH_3$ and $C_2H_5$. In an embodiment, R3 can be a linear hydrocarbon having seven to twenty seven carbons, in particular, fifteen to twenty carbons, or specifically seventeen carbons. In an embodiment, R4 can be $CH_3$ or H, while n is 1 to 100 or 1 to 5 and m is 1 to 10. In an embodiment, M can be Si or Sn. In an embodiment, R5 and R6 can each be independently selected from H, a substituted or unsubstituted aliphatic group (e.g., an alkyl group (e.g., $CH_3$, $C_2H_5$, $CH_2CF_3$)), a substituted or unsubstituted aryl group (e.g., $C_6H_6$), or and a substituted or unsubstituted heteroaryl group. In addition, R5 and R6 can each be independently selected from X, as described above, and a linker moiety (the compound above without Q), such as one described herein. Subscript p is 1 to 100. A bond to AM can be formed at the N of the $H_2N^+$ side of the first structure above.

In an embodiment, an article can include one or a plurality of types of antimicrobial moieties. In an embodiment, the antimicrobial moiety can be represented by:

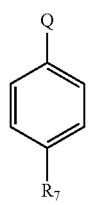

Q is defined above. In an embodiment, R7 can be defined as:

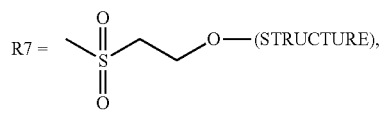

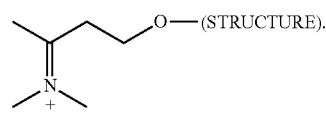

In an embodiment, the (STRUCTURE) can include the surface of the article or a functionalized layer on the surface of the article. In an embodiment, the surface or the functionalized layer includes —OH groups.

In regard to the discussion herein including the Examples above and the claims, it should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

The invention claimed is:

1. A compound, comprising an antimicrobial moiety having a structure:

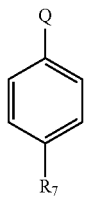

wherein Q is X; wherein R7 is selected from the group consisting of:

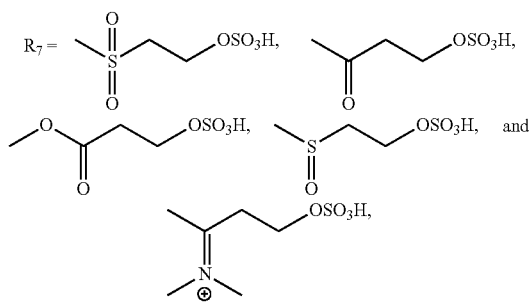

wherein X is an antimicrobial agent (AM).

2. The compound of claim 1, wherein the AM is selected from one or a combination of:

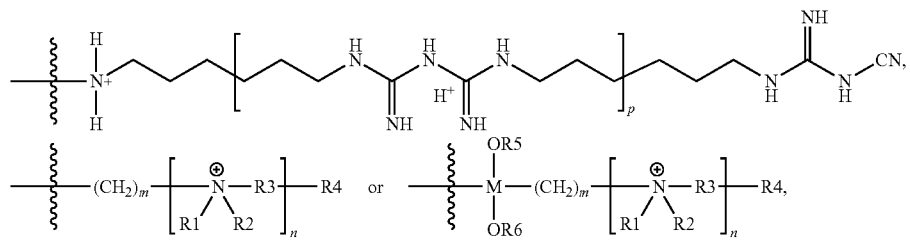

wherein R1 and R2 are each independently selected from H, a substituted or unsubstituted aliphatic group, a substituted or unsubstituted aryl group, and a substituted or unsubstituted heteroaryl group, R3 is a linear hydrocarbon having seven to twenty seven carbons, R4 is $CH_3$ or H, while is n is 1 to 100 and m is 1 to 10; M is Si or Sn; where R5 and R6 are independently selected from the group consisting of: H, a substituted or unsubstituted aliphatic group, a substituted or unsubstituted aryl group, a substituted or unsubstituted heteroaryl group, and another antimicrobial group, and p is 1 to 100, where a bond to AM is formed at the N of the $H_2N^+$ side of the first structure above.

3. The compound of claim 1, wherein $R_7$ is:

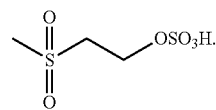

4. The compound of claim 1, wherein $R_7$ is:

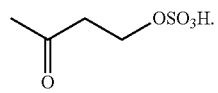

5. The compound of claim 1, wherein $R_7$ is:

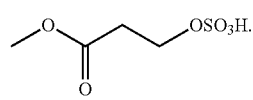

6. The compound of claim 1, wherein $R_7$ is:

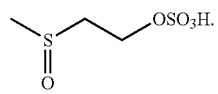

7. The compound of claim 1, wherein $R_7$ is:

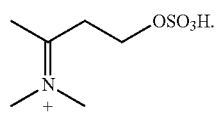

8. An article, comprising an antimicrobial moiety bonded to the article, wherein the antimicrobial moiety is represented by:

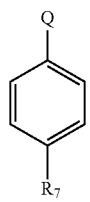

wherein Q is X; wherein R7 is selected from the group consisting of:

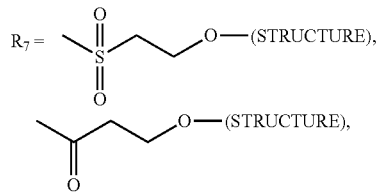

-continued

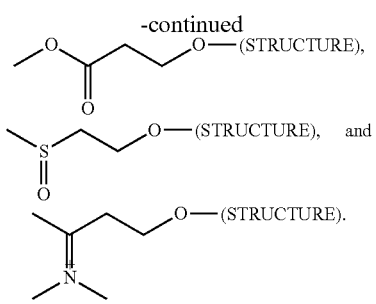

9. The article of claim 8, wherein the AM is selected from one or a combination of:

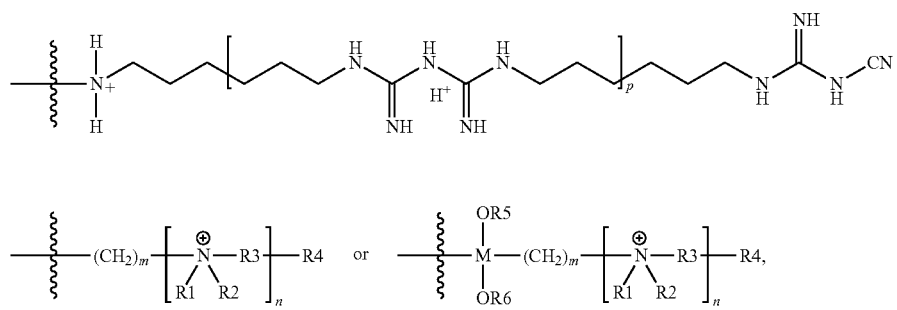

wherein R1 and R2 are each independently selected from H, a substituted or unsubstituted aliphatic group, a substituted or unsubstituted aryl group, and a substituted or unsubstituted heteroaryl group, R3 is a linear hydrocarbon having seven to twenty seven carbons, R4 is $CH_3$ or H, while is n is 1 to 100 and m is 1 to 10; M is Si or Sn; where R5 and R6 are independently selected from the group consisting of: H, a substituted or unsubstituted aliphatic group, a substituted or unsubstituted aryl group, a substituted or unsubstituted heteroaryl group, and another antimicrobial group, and p is 1 to 100, where a bond to AM is formed at the N of the $H_2N^+$ side of the first structure above.

10. The article of claim 9, wherein $R_7$ is:

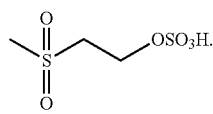

11. The article of claim 9, wherein $R_7$ is:

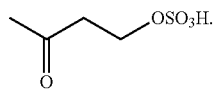

12. The article of claim 9, wherein $R_7$ is:

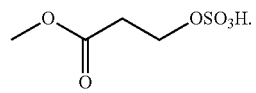

13. The article of claim 9, wherein $R_7$ is:

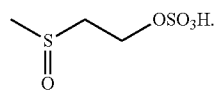

14. The article of claim 9, wherein $R_7$ is:

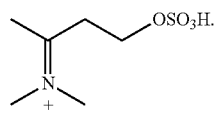

15. The article of claim 9, wherein the article includes a fiber made of a material selected from the group consisting of: a cellulose-based material, polypropylene, polyethylene, polyester, polyamide, aramid, and a natural fiber.

16. The article of claim 9, wherein the article is a textile article.

17. The article of claim 9, wherein the article is selected from the group consisting of: a counter top, processing equipment, a utensil, a food packaging material, a metal, a plastic structure, a medical instrument, a medical implant, a diaper, leather, and flooring.

* * * * *